US010589108B2

(12) United States Patent
Radziemski et al.

(10) Patent No.: US 10,589,108 B2
(45) Date of Patent: Mar. 17, 2020

(54) MINIATURIZED WIRELESS ULTRASOUND ENERGY TRANSFER SYSTEM FOR POWERING A BIO-IMPLANTABLE MEDICAL DEVICE

(71) Applicant: Piezo Energy Technologies LLC, Tucson, AZ (US)

(72) Inventors: Leon J. Radziemski, Tucson, AZ (US); Inder Raj Singh Makin, Mesa, AZ (US); Harry Jabs, Oakland, CA (US); Juan Carlos Lopez Tonazzi, Tucson, AZ (US)

(73) Assignee: Piezo Energy Technologies LLC, Tucson, AZ (US)

( * ) Notice: Subject to any disclaimer, the term of this patent is extended or adjusted under 35 U.S.C. 154(b) by 0 days.

(21) Appl. No.: 16/287,572

(22) Filed: Feb. 27, 2019

(65) Prior Publication Data

US 2019/0192865 A1    Jun. 27, 2019

Related U.S. Application Data

(62) Division of application No. 15/587,815, filed on May 5, 2017, now Pat. No. 10,252,066.
(Continued)

(51) Int. Cl.
*A61N 1/00*  (2006.01)
*A61N 1/378*  (2006.01)
(Continued)

(52) U.S. Cl.
CPC ........... *A61N 1/3787* (2013.01); *A61N 1/025* (2013.01); *A61N 1/37223* (2013.01);
(Continued)

(58) Field of Classification Search
CPC .. A61N 1/3787; A61N 1/37223; A61N 1/025; H02J 50/15; A61B 5/4041; A61B 2560/0219
See application file for complete search history.

(56) References Cited

U.S. PATENT DOCUMENTS 8,082,041 B1    12/2011 Radziemski
8,364,276 B2    1/2013 Willis
(Continued)

OTHER PUBLICATIONS

H. Basaeri et al., "A review of acoustic power transfer for bio-medical implants", Smart Materials and Structures, 2016, No. 25, IOP Publishing Ltd., UK.
(Continued)

*Primary Examiner* — Mallika D Fairchild
(74) *Attorney, Agent, or Firm* — Intrinsic Law Corp.

(57) ABSTRACT

A system for providing energy to a bio-implantable medical device includes an acoustic energy delivery device and a bio-implantable electroacoustical energy converter. The acoustic energy delivery device generates acoustic energy with a multi-dimensional array of transmitting electroacoustical transducers. The acoustic energy is received by one or more receiving electroacoustical transducers in the bio-implantable electroacoustical energy converter. The receiving electroacoustical transducers convert the acoustic energy to electrical energy to power the bio-implantable medical device directly or indirectly. An external alignment system provides lateral and/or angular positioning of an ultrasound energy transmitter over an ultrasound energy receiver. The acoustic energy transmitter alignment system comprises either or both x-y-z plus angular positioning components, and/or a substantially multi-dimensional array of transmitters plus position sensors in both the transmitter and receiver units.

22 Claims, 14 Drawing Sheets

Related U.S. Application Data

(60) Provisional application No. 62/332,100, filed on May 5, 2016.

(51) Int. Cl.
    *A61N 1/372*        (2006.01)
    *A61N 1/02*         (2006.01)
    *H02J 50/15*        (2016.01)
    *A61B 5/00*         (2006.01)

(52) U.S. Cl.
    CPC .............. *H02J 50/15* (2016.02); *A61B 5/4041* (2013.01); *A61B 2560/0219* (2013.01)

(56) References Cited

U.S. PATENT DOCUMENTS

| | | | |
|---|---|---|---|
| 8,594,806 | B2 | 11/2013 | Cowley et al. |
| 8,718,773 | B2 | 5/2014 | Willis et al. |
| 8,974,366 | B1 | 3/2015 | Radziemski et al. |
| 9,199,096 | B2 | 12/2015 | Lewis, Jr. |
| 9,480,863 | B2 | 11/2016 | Lewis, Jr. et al. |
| 9,492,687 | B2 | 11/2016 | Lewis, Jr. |
| 2004/0172083 | A1 | 9/2004 | Penner |
| 2005/0251044 | A1 | 11/2005 | Hoctor et al. |
| 2008/0294208 | A1 | 11/2008 | Willis et al. |
| 2008/0312720 | A1* | 12/2008 | Tran ................... A61N 1/3787 607/61 |
| 2009/0228072 | A1 | 9/2009 | Coe et al. |
| 2011/0275963 | A1 | 11/2011 | Wagner et al. |
| 2013/0178915 | A1 | 7/2013 | Radziemski et al. |
| 2016/0015972 | A1 | 1/2016 | Hyde et al. |
| 2016/0302692 | A1 | 10/2016 | Demmer |

OTHER PUBLICATIONS

B. Cotte et al., "Theoretical Study for Safe and Efficient Energy Transfer to Deeply Implanted Devices Using Ultrasound", IEEE Transactions on Ultrasonics, Ferroelectrics, and Frequency Control, Aug. 2012, p. 1674-1686, vol. 59, No. 8, IEEE.

M. Langer et al., "Hydrogel Materials as Ultrasound Coupling Media", American Institute of Ultrasound in Medicine Proceedings, J. Ultrasound Med, 2013, p. 539, 32(suppl.):S1-S134.

G. K. Lewis JR. et al., "Design and Evaluation of a Wearable Self-Applied Therapeutic Ultrasound Device for Chronic Myofascial Pain", Ultrasound in Med. & Biol., 2013, p. 1429-1439, vol. 39, No. 8, Elsevier.

Inder Raj S. Makin et al., "Miniaturized Ultrasound Arrays for Interstitial Ablation and Imaging", Ultrasound in Med. & Biol., 2005, pp. 1539-1550, vol. 31, No. 11, World Federation for Ultrasound in Medicine & Biology, USA.

T. D. Mast et al., "Bulk ablation of soft tissue with intense ultrasound: Modeling and experiments", Oct. 4, 2005, pp. 2715-2724, vol. 118, No. 4, Acoustical Society of America.

Changki MO et al., "Effect of misalignment between ultrasound piezoelectric transducers on transcutaneous energy transfer", Active and Passive Smart Structures and Integrated Systems, 2013, vol. 8688, 868814, SPIE.

C. Nistorica et al., "Characterization of a 3D-MEMS Piezoelectric Transducer for Portable Imaging Systems", IEEE International Ultrasonics Symposium Proceedings, 2015, 978-1-4799-8182, IEEE.

J. Norman et al., "Ultrasonic Dry Coupling Through Tissue", Journal of the Canadian Acoustical Association, 2015, vol. 43, No. 3.

S. Ozeri et al., "Ultrasonic transcutaneous energy transfer for powering implanted devices", Ultrasonics, 2010, p. 556-566, vol. 50, Elsevier.

S. Ozeri et al., "Simultaneous backward data transmission and power harvesting in an ultrasonic transcutaneous energy transfer link employing acoustically dependent electric impedance modulation", Ultrasonics, 2014, p. 1929-1937, vol. 54, Elsevier.

M. Peisino, "Deeply implanted medical device based on a novel ultrasonic telemetry technology", École Polytechnique Federale de Lausanne, 2013, Theses No. 5730.

A.F. Prokop et al., "Polyacrylamide Gel as an Acoustic Coupling Medium for Focused Ultrasound Therapy", Ultrasound in Med. & Biol., 2003, pp. 1351-1358, vol. 29, No. 9, Elsevier.

L. Radziemski et al., "In vivo demonstration of ultrasound power delivery to charge implanted medical devices via acute and survival porcine studies", Ultrasonics, 2016, p. 1-9, vol. 64, Elsevier.

S. Suzuki et al., "Fundamental study of an electric power transmission system for implanted medical devices using magnetic and ultrasonic energy", J Artif Organs, 2003, p. 145-148, vol. 6., The Japanese Society for Artificial Organs.

B. Yochev et al., "Investigation of Ultrasonic Properties of Hydrophilic Polymers for Dry-coupled Inspection", ECNDT, Technical University—Sofia, Bulgaria, 2006, p. 1-10.

\* cited by examiner

Steered power vs number of array elements for a 25 mm diameter transmitter and receiver pair.

MINIATURIZED WIRELESS ULTRASOUND ENERGY TRANSFER SYSTEM FOR POWERING A BIO-IMPLANTABLE MEDICAL DEVICE

CROSS-REFERENCE TO RELATED APPLICATIONS

This application is a division of U.S. patent application Ser. No. 15/587,815, titled "Miniaturized Wireless Ultrasound Energy Transfer System for Powering a Bio-Implantable Medical Device," filed May 7, 2017, which claims priority to U.S. Provisional Application No. 62/332,100, titled "Miniaturized Wireless Ultrasound Energy Transfer Source Using a Combination of Positioning and Alignment Methods," filed on May 5, 2016, both of which are hereby incorporated by reference.

STATEMENT REGARDING FEDERALLY SPONSORED RESEARCH OR DEVELOPMENT

This invention was made with government support under grant number R43 EB019225 awarded by the National Institutes of Health. The government has certain rights in the invention.

TECHNICAL FIELD

The present application relates to the ultrasonic transmission of electrical power between electronic devices.

BACKGROUND

Implantable electronic medical devices represent a large and growing commercial market. The lifetime of implanted electronic medical devices is typically limited by the life of their primary (non-rechargeable) batteries. Replacing them requires a costly procedure to remove the previously implanted medical device and replace it with another that contains new primary batteries. The surgery also introduces the risk of infection.

Rechargeable batteries carry the promise of a longer overall lifetime for many applications, reducing the number of such procedures, hence the costs in money and trauma to the patient. The lifetime of a permanent implanted battery, perhaps 7-10 years, may be adequate for some applications. But in pain neurostimulators and combination pacemakers-defibrillators, the batteries are discharged faster, sometimes depleting their batteries in 1-3 years. Moreover, children and young adults who get these implants will face many more permanent battery replacements, so even incremental increases in implant lifetime will be useful.

U.S. Pat. No. 8,082,041 (Radziemski) (incorporated herein by reference) describes an ultrasound system suitable for providing power to implanted devices such as pacemakers, defibrillators, and neurostimulators, and sensors primarily to recharge implanted batteries, however with the capability of also delivering power directly to an application. Batteries for such low power devices may be charged for periods of minutes to hours at rates that vary from once per day to once per week or month, or even less frequently. The aforesaid patent also contains a description of medical ultrasound power transmission.

Several methods for providing data for alignment of transmitter and receiver are taught in Radziemski. Typically, in those prior systems the alignment would be performed manually, by physically adjusting the orientation of the external transmitter unit in response to the data provided.

U.S. Pat. No. 8,974,366 (Radziemski and Makin) (incorporated herein by reference), discloses a full-time energy delivery ultrasound method to a storage device or directly to an application, plus a full-time non-mechanical alignment system.

Willis (US2008/0294208), incorporated herein by reference, teaches a two-dimensional ultrasound array to scan and search for a receiver located in or on the heart, to wirelessly provide pacing level voltages to the heart. Willis (U.S. Pat. No. 8,364,276), incorporated herein by reference, estimates the energy per pacing pulse provided as 0.17 micro Joules in a 0.5 millisecond pulse. Assuming a pulse rate of 60 per second, this converts to an average power of 0.17 micro Watts.

SUMMARY

Example embodiments described herein have innovative features, no single one of which is indispensable or solely responsible for their desirable attributes. The following description and drawings set forth certain illustrative implementations of the invention in detail, which are indicative of several exemplary ways in which the various principles of the invention may be carried out. The illustrative examples, however, are not exhaustive of the many possible embodiments of the invention. Without limiting the scope of the claims, some of the advantageous features will now be summarized. Other objects, advantages and novel features of the invention will be set forth in the following detailed description of the invention when considered in conjunction with the drawings, which are intended to illustrate, not limit, the invention.

An aspect of the invention is directed to a system for providing energy to a bio-implantable medical device, the system comprising: an acoustic energy delivery device configured to be secured to a patient's skin and apposed superficial tissue and a bio-implantable electroacoustical energy converter configured to be electrically coupled to the bio-implantable medical device, the bio-implantable electroacoustical energy converter coupled to the patient's skin tissue. The acoustic energy delivery device comprises a delivery device housing; a multi-dimensional array of transmitting electroacoustical transducers disposed on or in the delivery device housing, the multi-dimensional array of transmitting electroacoustical transducers arranged in a substantially regular two-dimensional geometric shape; a signal generator and power output board disposed in the delivery device housing, the signal generator in electrical communication with the multi-dimensional array of transmitting electroacoustical transducers; a microprocessor-based controller disposed in the delivery device housing, the microprocessor-based controller in electrical communication with the signal generator and the multi-dimensional array of transmitting electroacoustical transducers; and a battery disposed in the delivery device housing, the battery electrically coupled to the multi-dimensional array of transmitting electroacoustical transducers, the signal generator and power output board, and the microprocessor-based controller. The bio-implantable electroacoustical energy converter comprises a converter device housing; one or more receiving electroacoustical transducers disposed on or in the converter device housing, the one or more receiving electroacoustical transducers configured to convert acoustic energy received from the acoustic energy delivery device into converted electrical energy; and an energy rectification and storage device disposed in the converter device housing, the energy storage device in electrical communication with the one or more receiving electroacoustical transducers to store at least a portion of the converted electrical energy.

In one or more embodiments, the bio-implantable electroacoustical energy converter further comprises a microcontroller disposed in the converter device housing. In one or more embodiments, the system further comprises a wireless feedback loop between the bio-implantable electroacoustical energy converter and the acoustic energy delivery device. In one or more embodiments, the microcontroller is configured or programmed to modulate an impedance of the one or more receiving electroacoustical transducers to form the wireless feedback loop. In one or more embodiments, the microcontroller is configured or programmed to modulate an electrical load on a charging circuit that electrically couples the one or more receiving electroacoustical transducers to the energy storage device. In one or more embodiments, the acoustic energy delivery device further comprises a first RF antenna and the bio-implantable electroacoustical energy converter further comprises a second RF antenna, the wireless feedback looped formed by RF communication between the first and second RF antennas.

In one or more embodiments, the system further comprises a programmable external controller in electrical communication with the acoustic energy delivery device. In one or more embodiments, the microprocessor-based controller is configured or programmed to adjust a relative phase of input signals generated by the signal generator to steer a beam of the ultrasonic energy. In one or more embodiments, the system further comprises first magnets disposed on the delivery device housing and second magnets disposed on the skin tissue or on the converter device housing, the first magnets having an opposite polarity to the second magnets to magnetically retain an alignment of the acoustic energy delivery device and the bio-implantable electroacoustical energy converter. In one or more embodiments, the system further comprises x-y-z and angular alignment mechanical devices to optimize alignment of transmitter transducer and receiver transducer faces. In one or more embodiments, the system further comprises an acoustically-transparent adhesive to secure the acoustic energy delivery device to the patient's skin. In one or more embodiments, the acoustic energy delivery device and the bio-implantable electroacoustical energy converter each comprise a gyroscope and an accelerometer. In one or more embodiments, the microprocessor-based controller receives angular position and translational position data from the gyroscope and the accelerometer in the acoustic energy delivery device and from the gyroscope and the accelerometer in the bio-implantable electroacoustical energy converter, the microprocessor-based controller configured or programmed to adjust a relative phase of input signals generated by the signal generator to steer a beam of the ultrasonic energy according to a relative angular position and a relative translational position of the bio-implantable electroacoustical energy converter with respect to the acoustic energy delivery device. In one or more embodiments, the system further comprises a dry acoustic coupling between the multi-dimensional array of transmitting electroacoustical transducers and the patient's skin. In one or more embodiments, the dry acoustic coupling comprises polyurethane, silicone, natural oils, fatty-acids, polyacrylamide, a lipophilic material, or a hydrophilic material. In one or more embodiments, the dry acoustic coupling includes a dynamic coupling to optimize impedance matching of the transmitting electroacoustical transducers to the dry coupling material.

Another aspect of the invention is directed to a method for providing power to bio-implanted medical device, the method comprising: securing an acoustic energy delivery device on a subject's skin tissue proximal to the bio-implanted medical device; generating acoustic energy with a multi-dimensional array of transmitting electroacoustical transducers on or in the acoustic energy delivery device; receiving the acoustic energy with one or more receiving electroacoustical transducers on or in a bio-implanted electroacoustical energy converter that is electrically coupled to the bio-implanted medical device; with the one or more receiving electroacoustical transducers, converting the acoustic energy into electrical energy; and providing the electric energy to the bio-implanted medical device.

In one or more embodiments, the method further comprises providing a wireless feedback signal from the bio-implanted electroacoustical energy converter to the acoustic energy delivery device, the wireless feedback signal corresponding to a magnitude of the acoustic energy received by the bio-implanted electroacoustical energy converter. In one or more embodiments, the acoustic energy delivery device adjusts an angular or lateral position of a beam of the acoustic energy based on the wireless feedback signal. In one or more embodiments, the acoustic energy delivery device adjusts a frequency of the acoustic energy based on the wireless feedback signal. In one or more embodiments, the feedback signal is provided by varying an acoustic impedance of the one or more receiving electroacoustical transducers. In one or more embodiments, the method further comprises adjusting a relative phase of input signals to the multi-dimensional array of transmitting electroacoustical transducers to steer a beam of the acoustic energy based on the wireless feedback signal.

BRIEF DESCRIPTION OF THE DRAWINGS

Further features and advantages of the present invention will be seen from the following detailed description and in connection with the accompanying drawings where like numerals depict like parts.

DETAILED DESCRIPTION

The present invention relates to systems for powering implanted medical devices directly or via stored energy. The invention has particular utility for systems for powering implanted medical devices requiring periodic delivery of electrical power for implanted applications such as a variety of neurostimulators or sensors. These will be described in connection with such utility, although other utilities are contemplated. The following describes several system and method embodiments of the present invention, including various preferred embodiments thereof. It should be understood that the present examples are provided by way of illustration of the invention, and are not intended to be exhaustive or limiting. Those skilled in the art will appreciate further aspects or equivalent implementations of the invention upon review of the present disclosure, all of which are intended to be contemplated by and included in this disclosure.

In an aspect, conveniently retaining alignment between transmitter and receiver can be a critical feature of power delivery to an implant, whether by ultrasonic or electromagnetic means. In a unique aspect, ultrasound power delivery can mitigate the effects of lateral and angular misalignment by non-mechanical electronic means via a two-dimensional array of piezoelectric elements, leading to a dynamic, hands-off, real-time, self-aligning system that does not require patient intervention. Also, the ultrasound beam, in the near field may not diverge significantly, hence losses due to depth of the implant are minimal. Both of these advantages accrue to ultrasound because of its wave nature, and the fact that for power transfer, the ultrasound wavelength at useful frequencies is much smaller than the dimensions of the ultrasound transducers. In electromagnetic power delivery the converse is true, discouraging the use of non-mechanical alignment.

The present disclosure refers to an Ultrasound Electrical power delivery system ("USer") that, in some embodiments, transmits $10^6$ times more power than described in the aforementioned prior art, continuously or with duty cycles of 30% up to 95%.

Figure 1A:
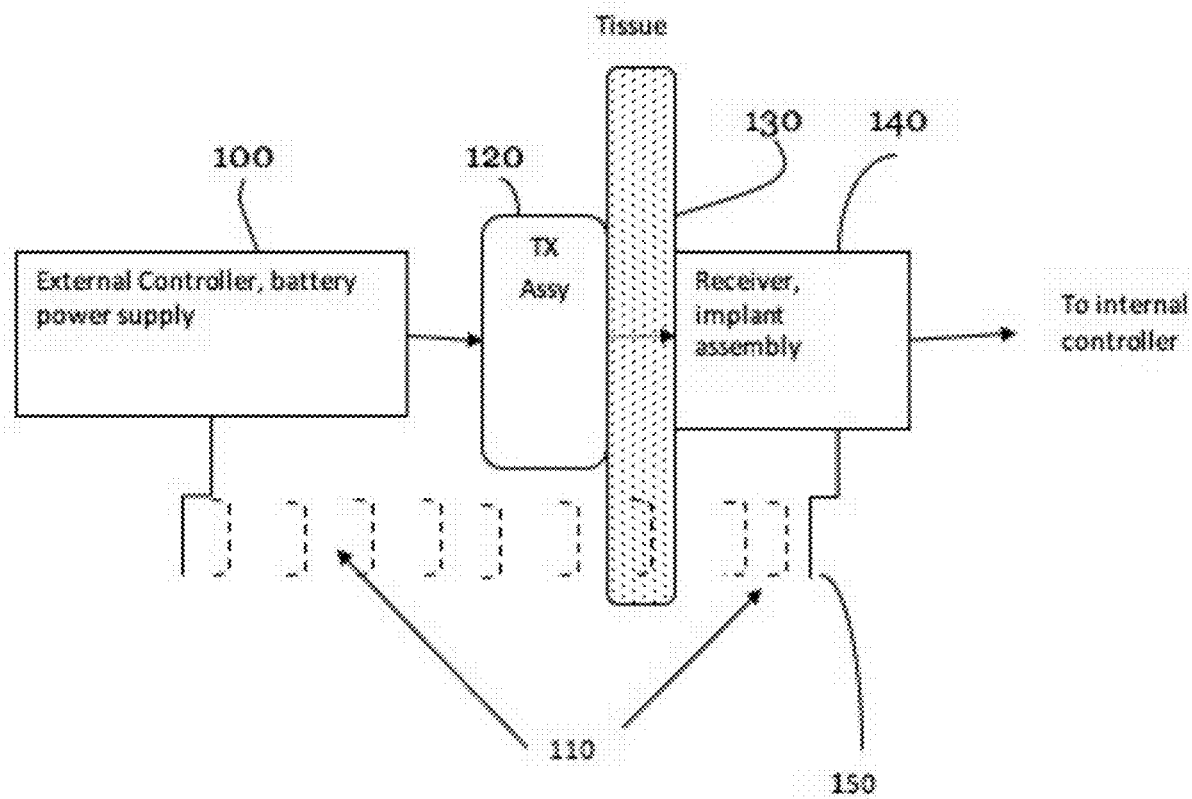
FIG. 1A is a schematic diagram of a USer system according to an embodiment.

FIG. 1A is a schematic diagram of a USer system according to an embodiment. The USer system includes an external controller 100 in electrical communication with a transmitter assembly 120 disposed on or adjacent to the subject's skin and apposed superficial tissue 130. In future reference to the "skin and apposed superficial tissue" within this specification, for simplicity, this tissue will be described as "skin." The transmitter assembly 120 includes one or more transmitting ultrasonic transducer elements to transmit ultrasound energy transcutaneously through tissue or skin 130 to an implant assembly 140. The implant assembly 140 includes one or more receiving ultrasonic transducer elements that receive the ultrasound energy and convert it into electrical energy to power an implanted medical device. The implanted medical device can be powered directly from the converted electrical energy or indirectly, for example via an energy storage device included in the implant assembly 140. Examples of such an energy storage device include a rechargeable battery, a capacitor, or other energy storage device.

The external controller 100 controls the level of input power and frequency of the ultrasound transmitter generated by transmitter assembly 120, bidirectional communication (e.g., between the external controller 100 and the transmitter assembly 120 and between the transmitter assembly 120 and the implant assembly 140), and if needed, the level of external cooling. The external controller 100 can also control an alignment feedback loop and/or an orientation optimization algorithm, as further discussed below. The transmitter assembly 120 and the implant assembly 140 each include an RF antenna 150 for bidirectional wireless RF communication 110 between the transmitter assembly 120 and the implant assembly 140. For example, the wireless RF communication 101 can be over the 405 MHz medical band, such as with a Zarlink or other brand of medical-band RF communication system. In addition, or in the alternative, bidirectional communication can be accomplished using the ultrasound energy (e.g., as discussed below).

The external controller 100 can be operated in two modes, manually and automatically, the latter via a feedback loop made possible by the wireless bidirectional communication between the transmitter assembly 120 and the implant assembly 140, which can have external and internal components. The output of the external controller 100 is connected to the transmitting assembly 120, which is disposed adjacent to the skin tissue 130 of the subject. In some embodiments, signals or data corresponding to the acoustic energy or power received by the implant assembly 140 is communicated to the transmitter assembly 120 using the feedback loop.

The transmitting ultrasonic transducer elements transmit acoustic energy via sine waves, square waves, triangular waves or an arbitrary repetitive shape. A cooling system may be deployed on or proximal to the transmitter assembly 120. During in vivo tests through 1-2 cm of tissue external cooling has been observed to penetrate the dermis, cooling the intervening tissue and the implant as well.

After penetrating the epidermis, dermis, and possibly fat and muscle layers, the ultrasound is incident on a biocompatible implanted container or housing which has the receiving ultrasonic transducer elements on or against the inside of the front face, and other elements packaged within it. The receiving ultrasonic transducer elements converts the ultrasonic to electrical energy, which is used to directly or indirectly power an implanted medical device. The implantable medical device and the implant assembly 140 can be combined in the same device or they can be separate devices that are electrically coupled.

Figure 1B:
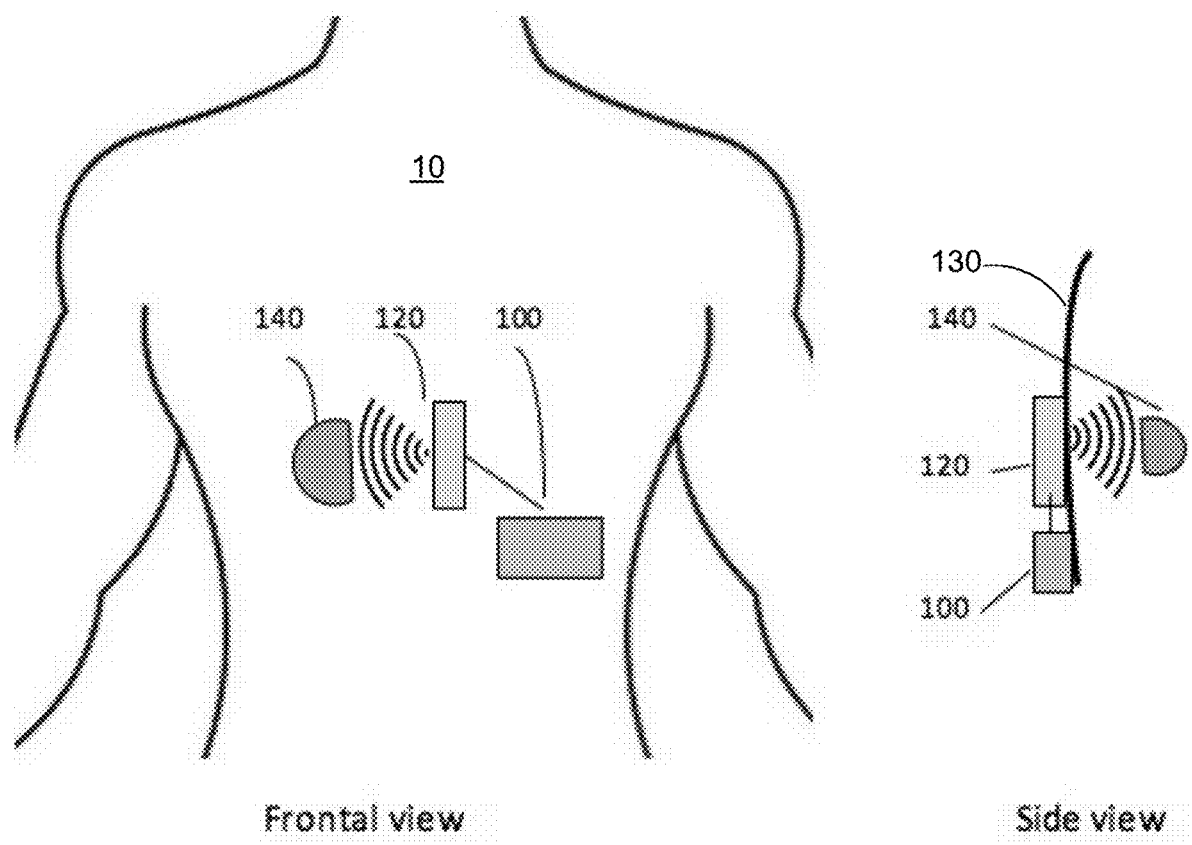
FIG. 1B illustrates the components of the USer system and their possible locations on the body or torso of a patient.

FIG. 1B illustrates the components of the USer system and their possible locations on the body or torso of a patient 10. The battery-powered controller and power supply 100 could be attached to a belt at waist level or as shown on the right of the torso. The transmitter assembly 120, electrically coupled to controller 100, resides up against the skin tissue 130 of the patient 10. An ultrasound beam 120 then relays power to the implant assembly 140, which is directly below (or across from) the transmitter assembly 120. The transmitting assembly 120 and implant assembly 140 may be positioned in various locations, on the upper chest below the clavicle, or lower on the belly, or to one side or slightly or completely toward the rear of the patient 10.

Figure 2:
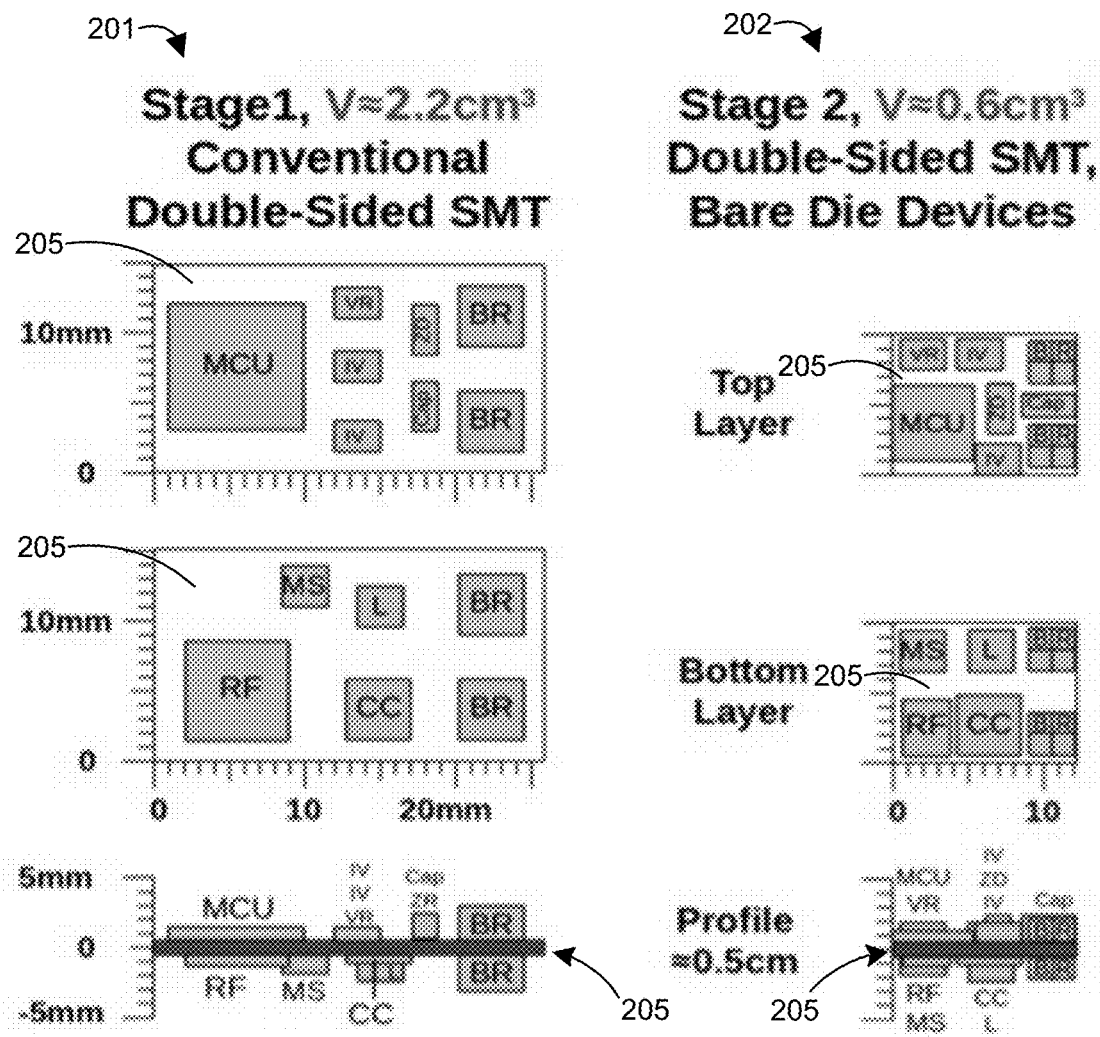
FIG. 2 shows two novel stages of miniaturization of the USer system with decreasing circuit size.

Implanted devices are becoming smaller and smaller in order to satisfy consumer demand and improve ease of implantation. Hence it is preferable that the circuitry and receiver element take up as small a volume as possible. FIG. 2 shows two novel stages 201 and 202 of miniaturization of the USer with decreasing circuit size. Some technological aspects that may be employed in one or more embodiments of the USer include: (a) surface-mount technology (SMT) to reduce printed circuit board (PCB) 205 size; (b) SMT with a double-sided PCB to further reduce areal and volumetric size; (c) bare dies instead of packaged devices and use wire die-bonding for interconnects to further reduce areal and volumetric size/weight; (d) multi-layer PCBs to route interconnections between components to further reduce PCB areal and volumetric size/weight; ability to accommodate wireless communications whether by RF or ultrasound.

Stage 2 202 achieves further novel miniaturization through use of a multi-layer printed circuit board (PCB) and smaller semiconductor device packages to develop a pre-production prototype. Wireless telecommunication compliant with the Medical Device Radio-Communications Service (MedRadio) can be implemented in the design of the USer. Wireless telecommunication can also comply with the international standard IEEE 802.15.6 for Wireless Body Area Network (WBAN) for reliability and security. To reduce the size, a total volume of the circuit may be kept under 0.8 $cm^3$, which is achieved in two stages. In the first stage 201 a PCB in surface-mount technology (SMT) is made with components spread out sufficiently to allow for modifications in the circuit having a volume of approximately 2.2 $cm^3$. In the second stage 202 the circuit is assembled in the highest practical density with double-sided component population of the PCB and wire-bonded bare die chips having an estimated volume of 0.8 $cm^3$. Again, these figures and examples are merely illustrative of the aspects of the present invention and are not intended to be limiting of it.

A substantial decrease in total circuit volume can be achieved by using bare die devices instead of packaged semiconductors. Each stage 201, 202 includes a PCB 205 on which a microcontroller (MCU), a voltage regulator (VR), current-to-voltage converters (IV), a Zener diode (ZD), a capacitor (Cap), bridge rectifiers (BR), a motion sensor (MS), an inductor (L), a charging circuit (CC), and a transceiver (RF) are disposed.

The stages 201, 202 of circuits on the PCBs 205 were drawn using the EAGLE computer-aided design tool (available from Autodesk, Inc.) to have 0.8 mm thin multi-layer boards made. After all connections were made, the circuit was cast in insulating epoxy to protect the delicate hardware and create a rugged module.

Figure 3:
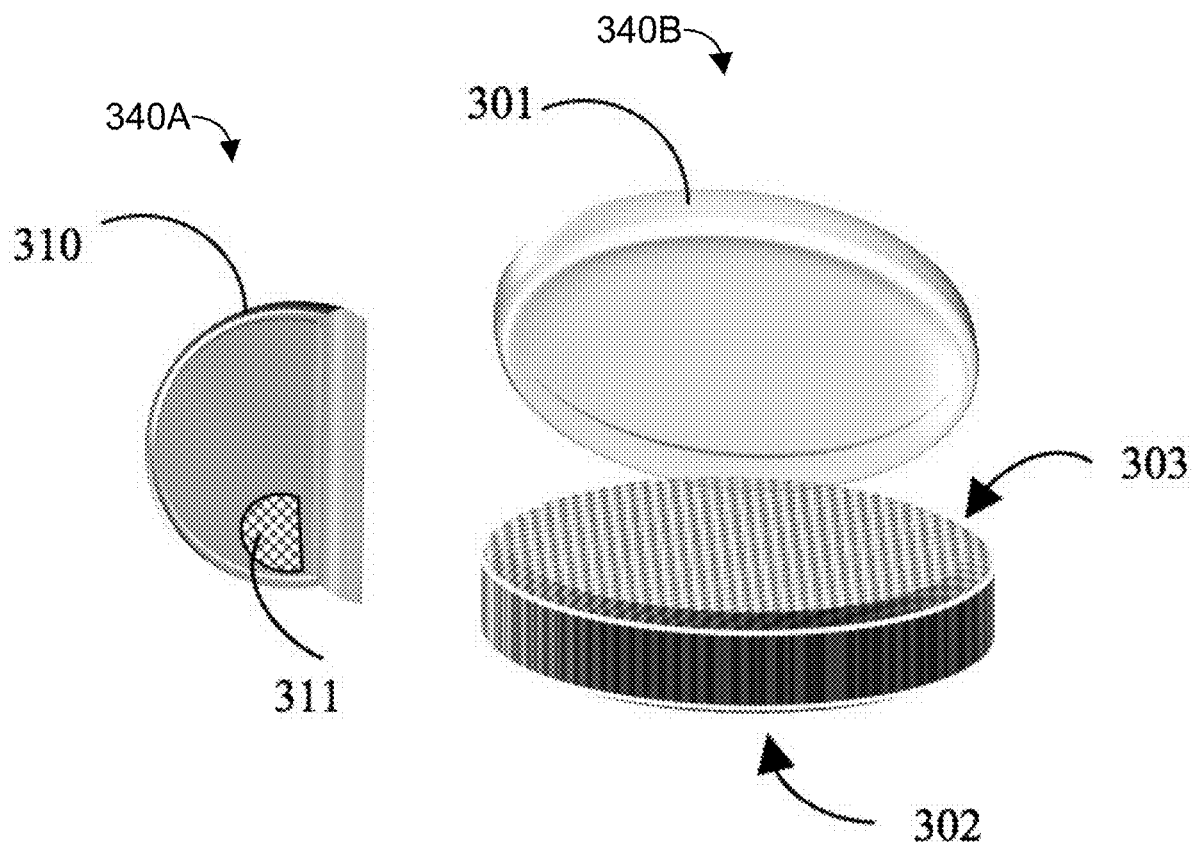
FIG. 3 illustrates the shrinking of the volume of the implant assembly by comparing two designs and of the implant assembly.

FIG. 3 illustrates the shrinking of the volume of the implant assembly by comparing two designs 340A and 340B of implant assembly 140. The volume reduction between designs 340A and 340B was more than a factor of 10. The newer, miniaturized implant assembly design container profile 310 is illustrated in design 340A on the left-hand side of FIG. 3, with electronics 311. Design 300B includes a two-piece puck-sized container with top 301 and bottom 303, inside of which is a much larger circuit board 302 containing the electronics.

The controller and RF transceiver chips in implant assembly 140 can provide ultra-low power consumption by offering a sleep-mode where current draw drops into the nano-Amp range to maximize battery life. The chips can be awakened to full functionality in less than 100 microseconds. Having an on-board microcontroller offers great flexibility for system control through the programming of the firmware.

Figure 4A:
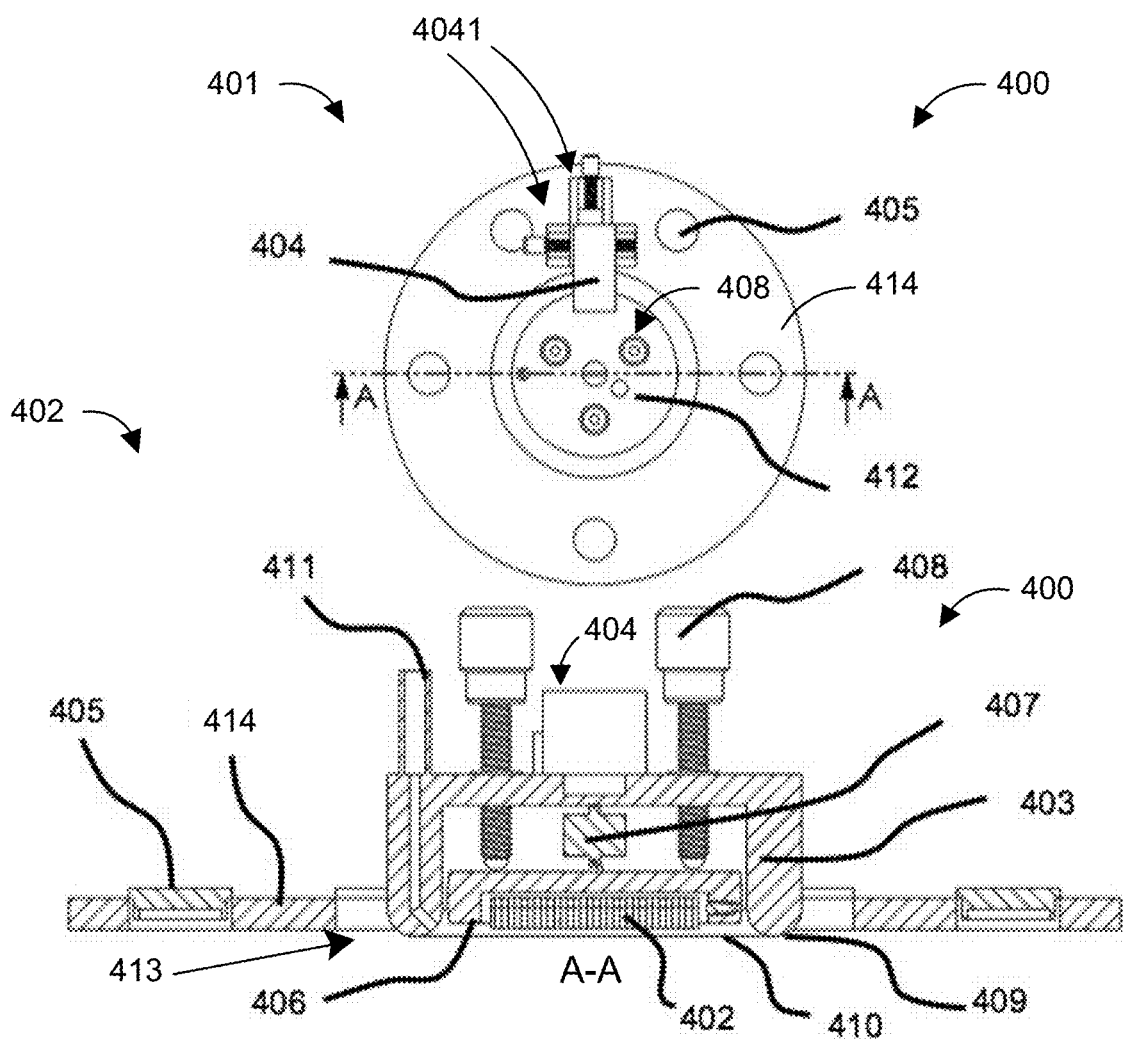
FIG. 4A illustrates a top view and a cross-sectional view of a novel transmitter apparatus that has these alignment mechanisms.

The transmitter unit of the ultrasound power delivery system can present the transmitter transducer to the skin with lateral, angular, and/or axial alignment mechanisms to optimize transmitter-receiver power transfer. FIG. 4A illustrates a top view 401 and a cross-sectional view 402 (through line A-A) of a novel transmitter apparatus 400 that has these alignment mechanisms, an earlier version of which has been used in animal tests.

The transmitter apparatus 400 includes lateral, angular, and axial alignment mechanisms attached to a cylindrical clamp 406. The transmitter apparatus 400 including transmitting transducers 402 are held in a cylindrical clamp 406 in which the transmitter apparatus 400 can be adjusted in the Z-axis by adjusting thumb screws 408, to create the optimal pressure on the subject's tissue. The clamp 406 is mounted with a pivot 407 to a frame 403. Frame 403 can be formed out of plastic (e.g., acrylic), aluminum, another material, or a combination of any of the foregoing. The three thumb screws 408 perform angular adjustment. The frame 403 is attached to an X-Y linear positioner 404, which allows for lateral adjustment of the transducer along the X- and Y-axes (in the x-y plane parallel to the skin surface of the subject). These axes are also user-adjustable in situ by thumb screws 4041. The X-Y linear positioner 404 is mounted on a frame 414 that matches the implant holder with magnets 405 of opposite polarity at the same positions on an implantable receiver unit collar. Frame 414 can be formed out of plastic (e.g., acrylic), aluminum, another material, or a combination of any of the foregoing. A large cross-shaped cutout 413 in the frame 414 accommodates a reasonable range of motion in the lateral-, and angular axes. The magnets 405 on the frame 414 and on the corresponding implantable receiver collar unit provide magnetic coupling and alignment between transmitter 400 and receiver units. For example, the magnets 405 on the frame 414 and on the implantable receiver collar unit are attracted to one another (due to opposite polarity). Such attractive magnetic force allows the transmitter unit 400 to maintain alignment with the receiver unit.

FIG. 4A illustrates the top of the transmitter apparatus 400 including the frame 414 to hold the transmitter apparatus 400 and the alignment magnets 405. The magnets 405 in the frame 414 can be arranged with alternating polarities (i.e., adjacent magnets 405 along the circumference of the frame 414 can have opposite polarities) to create a field line pattern that results in more attractive force compared to a pattern that has same polarities. The magnets 405 can protrude to a certain extent (e.g., 1-5 mm) from the frame 414 to bring their poles closer together for a more attractive magnetic force while maintaining the same distance between sending and receiving transducers elsewhere. Several geometries were tested. In one embodiment, the implantable receiver unit collar was slightly tapered to permit the magnets 405 to fit snugly into their holes. The magnets 405 may have a favorable geometry to produce the highest force-to-size/weight ratio. The magnets 405 may also be electromagnets whose strength can be varied.

The aforementioned magnetic method can be used over distances through which the transmitter and receiver unit magnets can act on one another, probably no more than a few (e.g., 0-3) centimeters. A more flexible non-magnetic method would be to affix the transmitter unit securely to one location, on the skin, directly over the receiver unit.

Figure 4B:
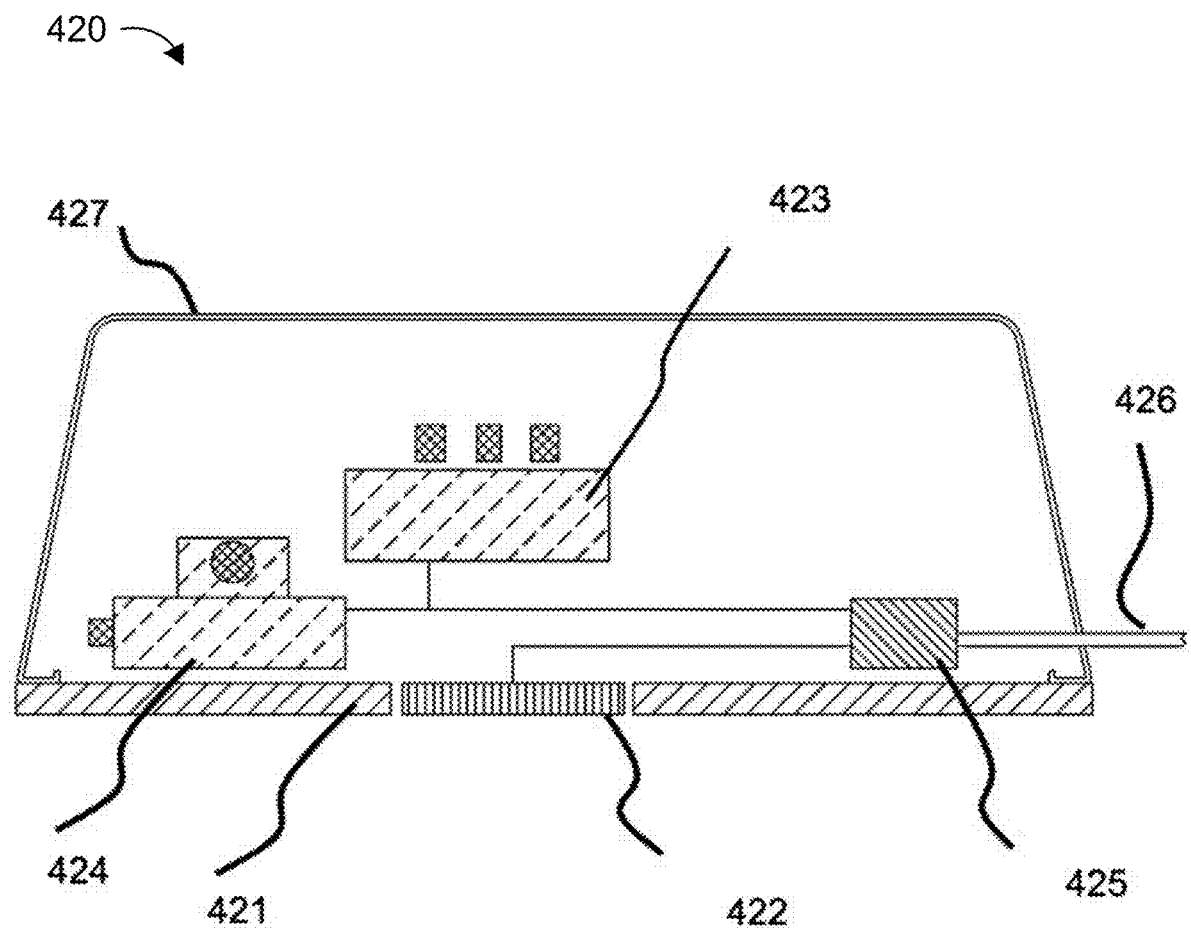
FIG. 4B illustrates an alternative embodiment for placing a transmitter apparatus securely over the receiver.

FIG. 4B shows an alternative embodiment for placing a transmitter apparatus 420 securely over the receiver. An adhesive 421 is disposed on the bottom of the transmitter 420 on either side of the transmitting transducers 422. The adhesive 421 can be disposed on a biocompatible and acoustically-transparent film, which is attached to the bottom of the transmitter apparatus 420. For example, the adhesive can cause the transmitter apparatus 420 to adhere and stay in place for four hours or more. Fabrico Inc. makes an example of this kind of biocompatible- and acoustically-transparent film, which for this application may include pressure-sensitive adhesive tapes for high strength medical bonds and gentle adhesion, precision die-cut adhesives, and select tape- and film-based adhesives for a variety of medical applications, all of which could be used in securing the transmitter unit 420 to the skin.

In addition, or in the alternative to using adhesive 421, the transmitter apparatus 420 can be secured with snaps such as those used when securing electrodes to the body for electrocardiograms. The female components on the bottom of the transmitter unit would be aligned with the male components on the skin (or vice versa), the latter being placed so as to position the transmitter approximately above the receiver. As is well known from the electrocardiogram application, this combination can keep a unit secured to the skin for up to 24 hours or even for days. In addition to the alternative using adhesive 421, one may combine the magnetic and adhesive methods. In this case, the magnets 405 in frame 414 can be paired with magnets of opposite polarity placed on top of the skin inserted into adhesive pockets which would replace the male snap components.

The embodiments described with respect to FIG. 4B have the advantage of securing the transmitter unit with a much lighter material and frame, thereby making that unit lighter and easier to manipulate.

However, a method of fine tuning the alignment both in translation and angularly is still required to achieve maximum efficiency of power transfer. FIG. 4B illustrates such a method, which itself has the virtue of being much lighter and easily manipulated than the one of FIG. 4A, which uses precision micrometers which unfortunately are heavy.

The transmitter apparatus 420 also includes a cover 427, a wire 426 connected to a power source (e.g., a battery, such as a battery in external controller 100). The transmitter apparatus 420 further includes stepper motors 423, 424, which can rotate and/or translate the transmitting transducers 422 (e.g., with respect to the X-Y plane), for example in response to the above-described feedback loop and/or detection of reflected power. The feedback can be processed by a microcontroller incorporated in the electronics module 425. An example of this feedback loop is described in U.S. Pat. No. 8,974,366 (e.g., in column 15), discussed above.

In addition, or in the alternative to the lightweight alignment systems of FIGS. 4A and 4B, phased ultrasound transducer arrays can be used to direct or steer the beam to the target receiver implant assembly. Ultrasound energy is most efficiently transferred when transmitting and receiving piezo transducers are properly aligned. Movements of the patient misalign the transducers, resulting in less than optimal energy transfer. Retaining alignment manually is stressful for the patient. There are two geometrical issues affecting alignment of a transmitter over a receiver in both the electromagnetic and ultrasound methods. The first is one- or two-dimensional lateral translation (e.g., in the X-Y plane parallel to the subject's skin) over the implant, and the second is one- or two-dimensional angular misalignment between the transmitter and receiver. With ultrasound, the use of a one- or two-dimensional transducer arrays in the transmitter apparatus enables compensation for either or both of these misalignments.

Figure 5:
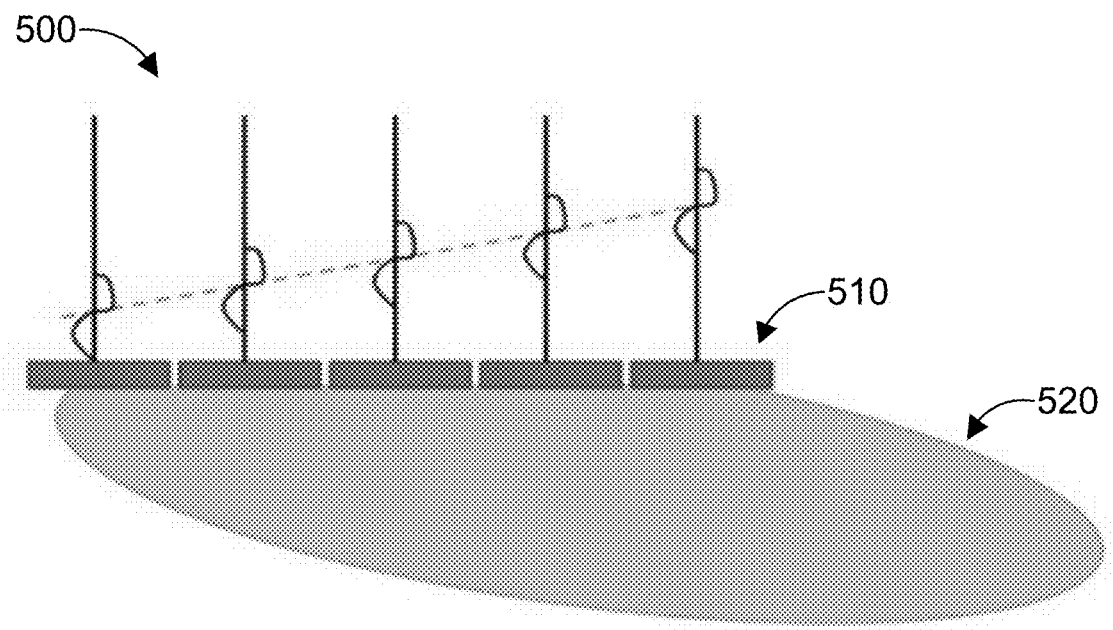
FIG. 5 illustrates an example of a phased transducer array and its ability direct or steer the generated acoustic (e.g., ultrasound) energy.

FIG. 5 illustrates an example of a phased transducer array and its ability direct or steer the generated acoustic (e.g., ultrasound) energy. The one-dimensional array 500 illustrated in FIG. 5 is a series of narrow piezo elements 510 in a row. When the same phase difference or time delay is introduced between each element 510, the beam 520 is deflected. A non-uniform phase difference can be used to generate a converging or diverging beam. A single array in the one- or two-dimensional transmitter may suffice, or a second one- or two-dimensional array in the receiver may be used to enhance the alignment. The degree of offset can be established by feedback from the implanted receiver signal and reduced power transfer (e.g., communicated through the feedback loop described above). Additionally, the misalignment can be gauged by the magnitude of the back reflected acoustic signal from the receiver surface.

Other materials may be used either in single element 510 or array 500 of transducers, such as magnetostrictive materials or capacitive microfabricated ultrasonic transducers (CMUTs). In one embodiment, a piezoelectric disk comprised of a ceramic matrix in which are embedded crystals of Lead-Zirconium-Titanate (PZT), also called a composite, can be the basis of one or more transducer elements 510. Other materials such as crystalline Lead-Magnesium-Niobate in Lead-Titanate (PMN-PT) may also be used.

Ultrasonic transducers micro-machined with semiconductor equipment offer the promise of size, weight, and cost reduction. A promising type of device is called a pMUT (piezoelectric micro-machined ultrasound transducer). These offer the potential to operate at much lower transmit voltages than transducers which rely on bulk piezoelectric material area. Transducers of other shapes, such as curved non-planar geometries can also be used to modify the directivity of transmitter ultrasound beam and/or receiver cone of beam acceptance.

Positioning electronics combined with ultrasound arrays can be used to optimize power delivery and generate hands-off, non-mechanical alignment. In an example, a pair of 9-axes angular and lateral position detectors (chips), such as gyroscopes and accelerometers, are placed in the implanted receiver as well as in the transmitted apparatus. Streaming orientation data from both sensors are compared in real-time to determine the translational and angular position of the piezo receiver with respect to the piezo transmitter. Once so determined, the phase difference corresponding to the displacements is entered into the beam-control software (e.g., in external controller 100) to position the beam in its optimum location. Slight dithering about that position may be used to confirm or further optimize the power transfer, because the intervening tissue medium can deflect the ultrasound beam slightly, and used for rapid adjustment of the ultrasonic wavefront to maintain optimal alignment.

Figure 6:
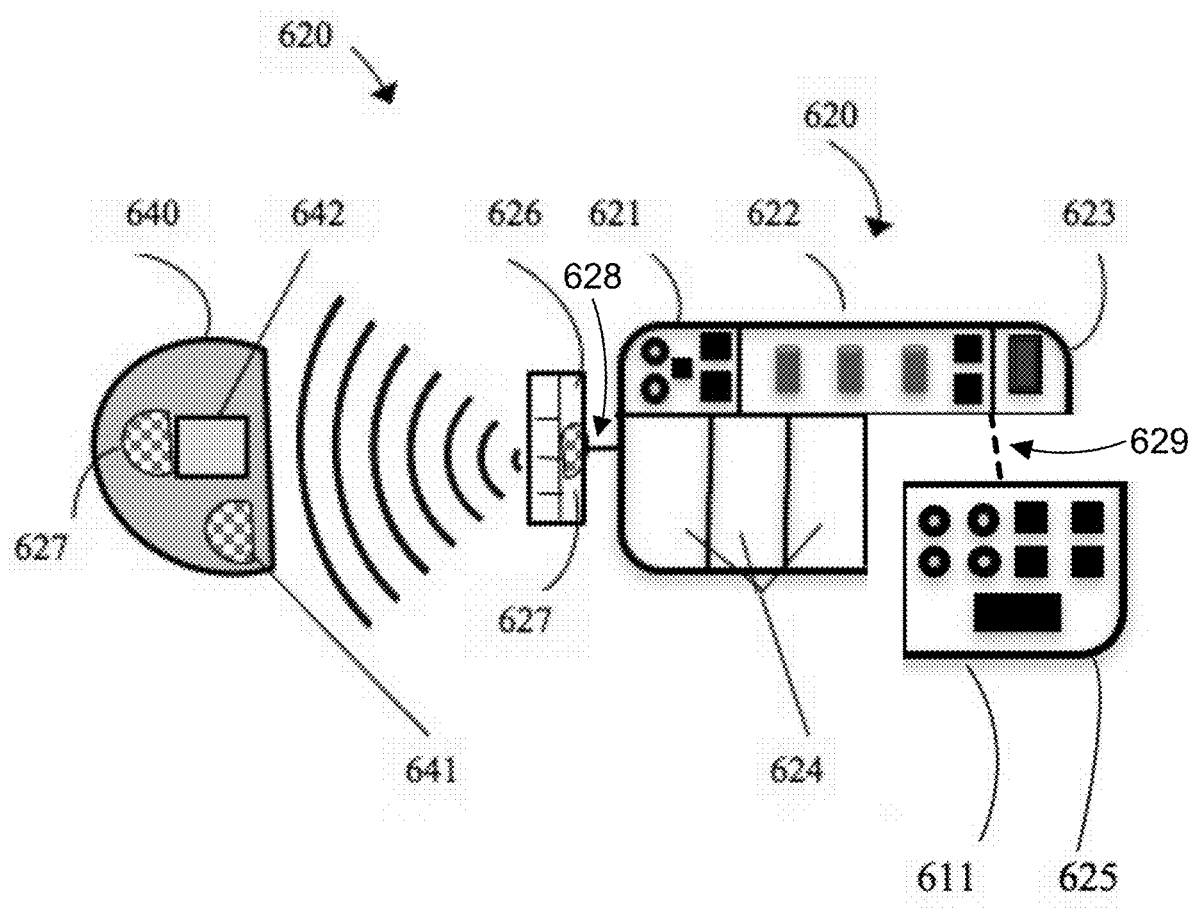
FIG. 6 is a schematic illustration of certain components in a system having a transmitter apparatus and an implanted receiver apparatus according to one or more embodiments.

FIG. 6 is a schematic illustration of certain components in a system 600 having a transmitter apparatus 620 and an implanted receiver apparatus 640 according to one or more embodiments. Transmitter apparatus 620 drives ultrasound piezo transmitters 626 which provides the ultrasound beam incident on the receiver 642. Beam direction is dynamically controlled in real-time by inputs from the sensors placed in the implant and the transmitter unit for optimal energy transfer and communication. Transmitter apparatus 620 includes a piezo driver 621, a signal generator 622, a wireless module 623, a battery pack 624, a microcontroller and power output board 625, and ultrasound piezo transmitters 626 attached by a flexible cable 628. The microcontroller board 625 includes a microcontroller and one or more position and/or orientation sensor readout(s). In addition, the microcontroller on microcontroller board 625 can control an accelerometer and/or a magnetometer in a positioning chip 627 in the transmitter 626. An example of a microcontroller board 625 of this type is the MPU-9250 chip from InvenSense, Inc. providing a minuscule package of only 3 mm×3 mm×1 mm (length×width×height). The microcontroller board 625 may be embedded in transmitter apparatus 620 by a flexible cable 629. In addition, or in the alternative, a second microcontroller board can be incorporated into the receiver electronics 641. The second microcontroller board includes a microcontroller that can control an accelerometer and/or a magnetometer in a positioning chip 627 in the receiver apparatus 640.

The accelerometer and/or the magnetometer can provide respective measurements (i.e., acceleration and magnetism, respectively) in up to 3 axes, for example, in the X-, Y-, and Z-directions in a Cartesian coordinate system. In some embodiments, the high-integrated microcontroller board 625 also includes signal conditioning circuits 611, analog-to-digital converters, a digital motion processor, and/or a serial interface 629 for an inter-integrated circuit (I2C) bus to communicate with the microcontroller. Note that microcontroller board 625 may be coupled to other circuit and system components as would be reasonably implemented by those skilled in the art and depending on the need at hand. For example, the board and/or processing circuit(s) can be integrated or separate from said other circuits and said system in various embodiments.

The combined data of these 9 axes (from the 3-axes accelerometer and the 3-axes magnetometer (also called a positioning chip)) make it possible to accurately determine the absolute and relative angular and lateral positions of the ultrasound piezo transmitters 626 and the ultrasound piezo receiver 642. Both transmitter 626 and receiver unit 640 would have one of the positioning chips 627 in it. These data can be input to the phased array of ultrasound piezo transmitters 626 to control beam steering and maintain optimal ultrasound energy transfer and bidirectional communication. The fast-responding electronics (sensor readout, signal processing, algorithm processing and actuation) in microcontroller board 625 have time constants much shorter than the physical movements of transmitter 626, subject, and implantable receiver 640, to effectively track optimal operating conditions with minimal dwell time in less-than-optimal operating conditions.

The implanted receiver apparatus 640 includes electronics 641 which can include a microprocessor, an ultrasound receiving transducer(s) 642, and a positioning chip 627. The ultrasound piezo receiver transducer(s) 642 is/are bonded to the face of the receiver apparatus. The positioning microchip 627 is disposed very close (e.g., less than 5 mm from) to the piezo element 642 so that it can provide accurate spatial position information.

The receiver circuit rectifies the 1 MHz sinusoidal signal from the receiver transducer. The circuit drives a charging chip, and conditions the received power to charge the secondary battery in a stable manner. In addition, functional and safety parameters, such as receiver impedance, multipoint temperature measurements as well as charging current and various tapped voltages within the charging circuit are constantly monitored within the Receiver apparatus 640. The Receiver apparatus 640 constantly (or frequently or nearly constantly) communicates with the transmitter apparatus 620 located outside the body. The aim of the circuit within the receiver apparatus 640 is to maintain an adequate charge in the secondary battery in order that the implant device can operate in a reliable and safe manner.

The controller 100 and/or transmitter apparatus 620 will have a simple rechargeable cell phone battery pack having adequate energy storage and a total volume half that of a standard cigarette pack. That stores ample energy to a) generate the 1 MHz drive frequency for the ultrasonic transducer, b) for ancillary electronics, and c) enough for a few charging cycles. The electronics include control and display capabilities as well as circuitry communicating with the implant and, during research or to download performance characteristics periodically, a laptop computer.

In one embodiment, the traditional USB cable will be replaced with a wireless Bluetooth dongle or internal (or external) Bluetooth antenna. A user control panel with digital display for key charging parameters is attached to the driver unit.

The controller 100 has several important functions. It may also be used to monitor and change the frequency of the ultrasound source. Typically, the range of changes are approximately 10% of the resonant frequency, and this is achieved via a variable frequency oscillator or a synthesized signal generator. The frequency can be set manually with an input command, or can be placed under the control of a frequency feedback loop.

Two other controller functions may include monitoring and aligning the transmitter and receiver faces non-mechanically, and energy management to regulate the heat removal needed for safe operation.

In an embodiment, the controller includes the electronics which enable reception of communications from the implant on a radio-frequency medical communication band, or acoustically from the transmitter unit. These comprise receiving values of temperatures being monitored in various implant locations, monitoring the efficiency of power conversion, and monitoring transmitter and receiver unit alignment. In one embodiment, a hybrid National Instruments Signal Express plus C++ code collects and stores the data automatically and continuously for up to 10 or even 20 parameters, both for patient information on a user interface and for periodic diagnostic downloading. The latter allows a variety of charts, comparisons, and figures of merit to be recorded and analyzed, to monitor the performance of the system.

Software compares the temperature readings with a preset regime of safe temperatures and, if necessary, sends a warning to a user interface, similar to a smart phone, which allows the patient to monitor power efficiency and control charging. The user interface communicates with the controller using a wireless protocol, such as Bluetooth, Wi-Fi, or other advanced method.

Figure 7:
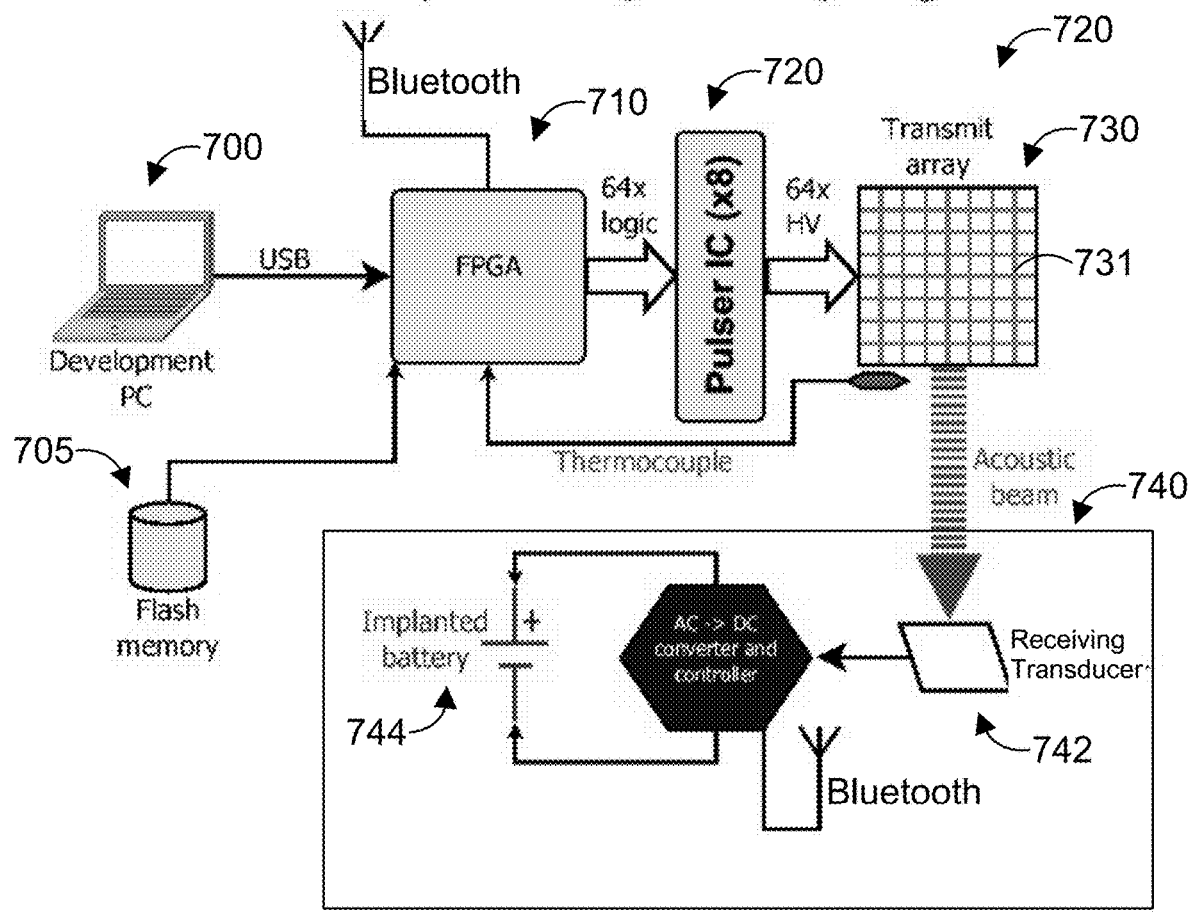
FIG. 7 illustrates the details of driving an array to produce beam steering and power transmission from a transmitter apparatus to an implantable receiver apparatus according to one or more embodiments.

FIG. 7 illustrates the details of driving an array to produce beam steering and power transmission from transmitter apparatus 720 to implantable receiver apparatus 740 according to one or more embodiments. The transmitting transducer 730 is comprised of an 8×8 array of 3 mm square piezoelectric elements 731. The multi-element 731 matrix in transmitting transducer 730 can be used to reduce or eliminate transducer misalignment, which can occur on two axes. Additionally, the transmitted beam can be focused by using variable phase algorithms well known to those experienced in the field.

The transmitting transducer 730 is controlled by FPGA 710 such as one produced by Altera or Xilinx. Development PCBs containing FPGAs and an interface to a PC are available inexpensively from vendors such as Opal Kelly Inc. In an aspect, FPGA 710 has several functions, including the generation of 64 logic outputs at 1 MHz, with signals of correct phases to maximize power transfer, for example to present a flat phase front to the receiving transducer 740, regardless of the relative orientation of the transmitting transducer 730 and the receiving transducers 740. These outputs are fed to a plurality of pulser ICs 720. An example of a suitable commercial pulser IC is the HV7350, an 8-channel design by Microchip Technology Inc. These pulser ICs 720 provide the level shifting and high voltage output stage suitable for driving the array of piezoelectric elements 731.

In addition, FPGA 710 controls timing for the start and stop of charging, and senses the temperature at the array surface using a thermocouple to discontinue operation if a fault condition occurs. Software for the FPGA is developed on a standard PC (e.g., development PC 700) and transferred to the FPGA's circuit board using a USB connection. The program for the FPGA 710 is stored in a flash memory device 705, whose contents (the "bit-file") are loaded into the FPGA 710 when power is first applied to the circuit. The FPGA 710 is in communication with an external controller (e.g., external controller 100), which provides commands and instructions for operation.

Another embodiment may incorporate a closed-loop system in which the receiver reports to the transmitter data on power transfer and alignment errors using Bluetooth, as indicated in FIG. 7. The FPGA 710 uses this data to alter the phases of its outputs, so that the power transfer is continuously maximized when the relative positions of the transducers are altered due to breathing, body motion, or other causes.

As discussed above, the implantable receiver apparatus 740 includes a receiving transducer 742 (referred to as receiving transducer 642 in FIG. 6) (that receives the acoustic (e.g., ultrasonic) energy transmitted from the transmitting transducer 730 and converts it into electrical energy to charge a battery 744 or directly power an implanted medical device. The battery 744 can be coupled to a rectifier (e.g., a bridge rectifier, as discussed above). The transmitter apparatus 720 and implantable receiver apparatus 740 can communicate via Bluetooth, another wireless communication device, or via ultrasound as discussed herein.

At an operating frequency of 1 MHz, the 3 mm square piezoelectric elements 731 are 2 wavelengths wide ($4\lambda^2$ area). This size was chosen to allow for the array to be steered by an angle of ±15 degrees without a large loss of main lobe energy. The array will exhibit grating lobes, especially at larger steering angles, but this is not anticipated to significantly interfere with the intended operation.

This transmitter design allows for detailed control of the emitted field, enabling a high level of system performance with a simple receiver. In one embodiment, the receiver is a single piezo element. In another embodiment it may be an array. The receiver design is preferably kept within the volume budget of the apparatus to satisfy the clinical requirements of the product. Choice of the appropriate array parameters can be facilitated by modeling of the transmitter beam forming and its interaction with the receiver. Modeling demonstrates an important point, the decreasing sensitivity to alignment of two plane parallel transducer faces.

Maximum power transfer takes place when the incoming wave is at the same phase at all points on the receiver. In order to keep the incoming wave from the transmitter in phase across the face of the receiver, the two must be aligned to within one-half wavelength, which for a frequency of 1 MHz in tissue is approximately 1 mm. This alignment condition becomes more and more stringent as the diameter of the transducers increases. In an embodiment, for a 10 mm diameter transducer, the alignment condition is that the two surfaces be parallel to 1 mm out of 10 mm. For a 70 mm diameter transducer, the condition is 1 mm out of 70 mm. This condition is relaxed for an array because the width of the array element substitutes for the overall width of the whole array. An array element width can vary from 0.1 mm to several millimeters in an exemplary embodiment.

Figure 8:
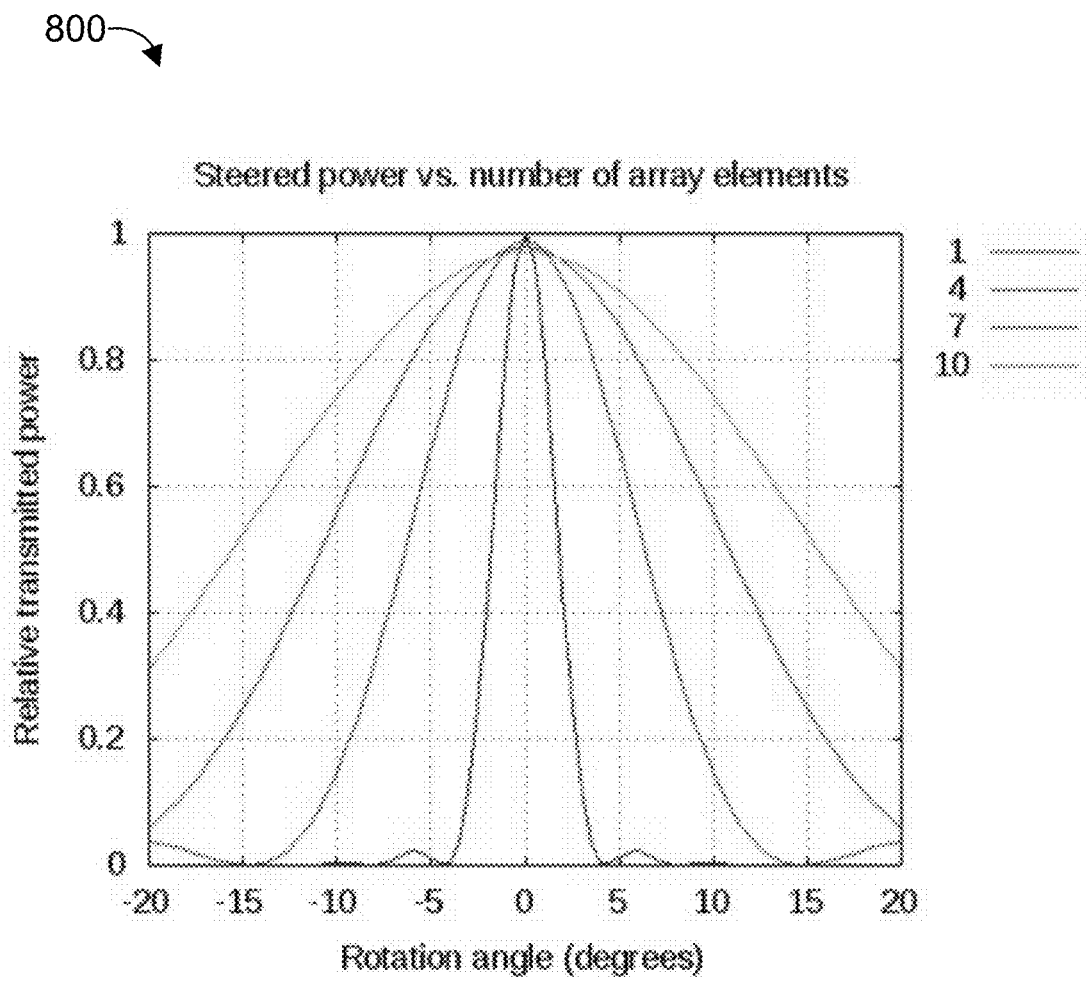
FIG. 8 is an exemplary model-based calculation result for an ultrasound frequency of 1 MHz and 25 mm diameter transducers.

This relaxation is shown in FIG. 8 in an exemplary model-based calculation result 800 for an ultrasound frequency of 1 MHz and 25 mm diameter transducers. Therein is plotted the steered power versus the number of array elements for a pair of 25 mm diameter transducers, where the transmitter is a one-dimensional array, and the receiver is a monolithic single element. The narrowest trace is for one element, and then follow in increasing width the traces for 4, 7, and 10 elements. For a single 25 mm diameter transmitter element (the whole transducer), the power falls to 80% with one degree of misalignment on either side of the center line. Increasing the number of elements per unit area to 10 spreads the 80% power cone to plus or minus 8 degrees (i.e., ±80°). That in turn, reduces the restriction on the angular alignment to retain 80% power to ±8° according to the foregoing exemplary embodiment.

As discussed above, a feedback loop can be provided between the transmitter and receiver devices. The feedback loop can provide non-mechanical, hands-off alignment of the transmitter and receiver devices.

Streaming orientation data from both sensors (e.g., accelerometer and magnetometer) will be compared in real-time and used for rapid adjustment of the ultrasonic wavefront to maintain optimal alignment. The block diagram in FIGS. 1A and 7 shows how the transmitter and receiver units are linked by a wireless feedback loop (e.g., Bluetooth). Alternatively, the feedback loop can be formed using the transmitted and/or received acoustic energy, as discussed below.

Figure 9:
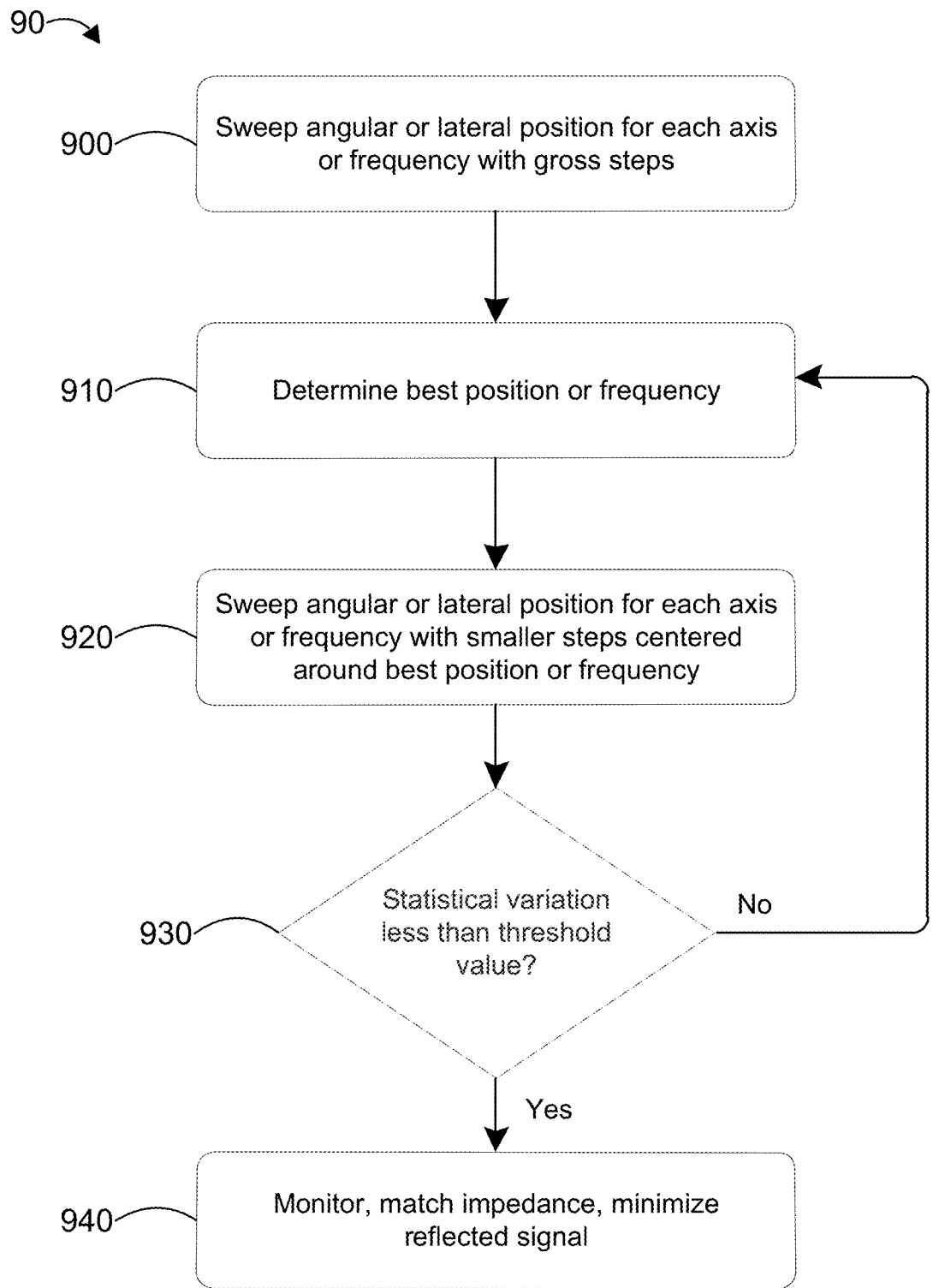
FIG. 9 is a flow chart that illustrates an exemplary feedback method used to optimize the position of each axis of the lateral and angular alignments, and the frequency from the signal generator.

FIG. 9 is a flow chart 90 that illustrates an exemplary basic feedback method used to optimize the position of each axis of the lateral and angular alignments, and the frequency from the signal generator. In step 900, the angular or lateral position for each axis or frequency is swept across its entire range with a gross step between each position or frequency, while measuring the level of the receiver power. Examples of the gross steps are: X-Y steps of ±2 mm; angular steps of ±2 degrees; and/or frequency steps of ±10 kHz. At each step the receiver power is calculated by the product of the voltage and current going to the battery, determined in the charging chip and relayed from the receiver unit to the controller, which then sets the next step. In step 910, an algorithm in the external controller determines where the highest power is achieved in the multi-dimensional surface composed of all position parameters plus the frequency. In step 920, the positions and frequency are again swept but across a smaller range centered around the optimum parameters from the gross step sweeps in step 900, but at a smaller step size on the order of 25% of the gross steps. For example, the smaller step size can include X-Y steps of ±0.5 mm; angular steps of ±0.5 degrees; and/or frequency steps of ±2.5 kHz. The flow chart 90 then returns to step 910 to determine the optimum parameters for highest level of power received by the implantable receiver at the smaller step size. This process is repeated using progressively smaller step sizes (e.g., each iteration through step 920 can have a step size of 25% of the prior iteration) until at step 930 the statistical variation is less than a threshold value, such as is inside error bars or within a predetermined variance. In step 940 the electroacoustic impedance is matched dynamically, by optimally coupling the matching layer between transducer and skin tissue.

Figure 10A:
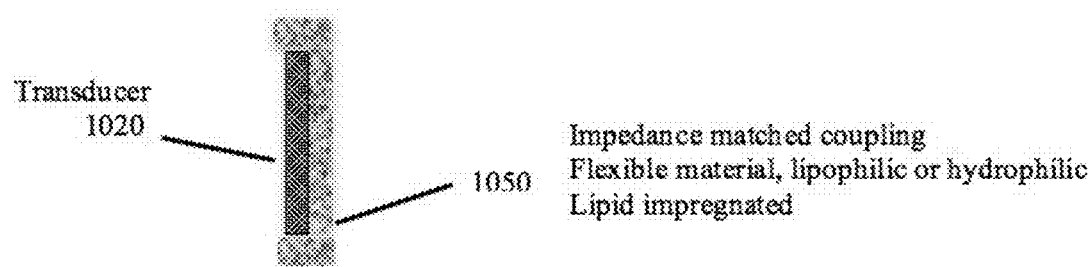
FIGS. 10A and 10B illustrate examples of a dry coupling medium.
Figure 10B:
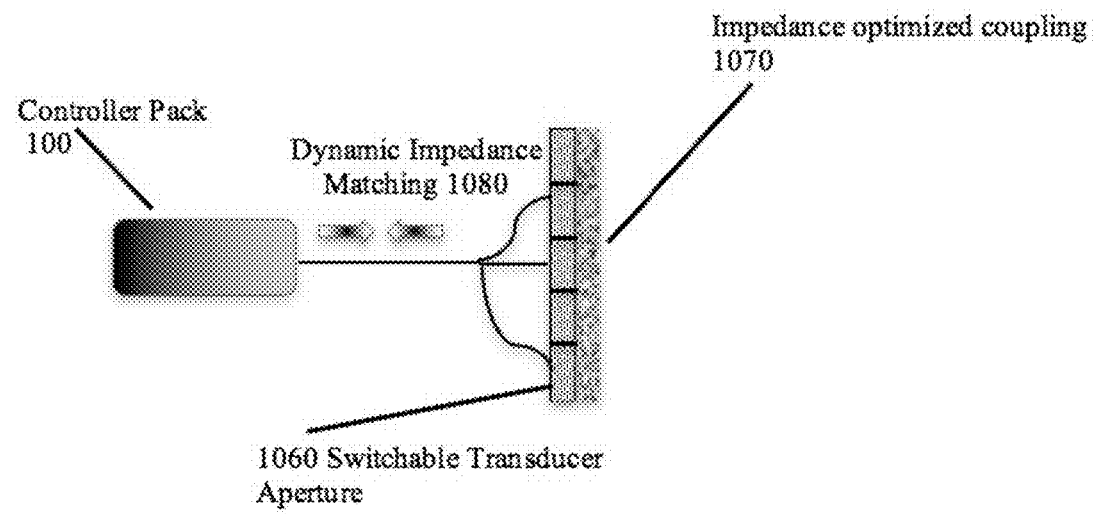

Individual power measurements may vary due to electronic noise effects. With gross steps, it is easy to measure distinct changes, but as the step size decreases, the noise floor quickly overcomes the differences in power created by a change in position or frequency. To get a finer step size and still be able to discern a clear change in power, an averaging of ten measurements is useful. In another embodiment, the averaged measurements can be filtered for each location and frequency. Similar fine alignment can be performed by optimizing the back reflected acoustic signal from the receiver surface by using a short scout-pulse prior to operating the system to power transfer mode, as well as intermittently between the charging phases In some aspects, the surface of the ultrasound transmitter can be designed such that a "dry application" on the skin tissue can be accomplished, without the existing "wet gel" used for medical ultrasound applications. FIGS. 10A and 10B illustrate examples of a dry coupling medium. FIG. 10A illustrates an example of an acoustic impedance-matched boot coupling 1050 for a transducer 1020. FIG. 10B illustrates a side view of a cross-section of a switchable transmitter transducer aperture 1060 to optimize acoustic energy delivery to an implant using an impedance optimized dry coupling 1070, along with dynamic tissue coupling feedback 1080 to external controller 100 to maximize acoustic energy delivery through tissue. The dry couplings 1050, 1070 may be useful for efficiently delivering acoustic energy from the acoustic source into the tissue. The dry couplings 1050, 1070 can include a polyurethane-based, silicone based, natural oils, fatty-acid based, polyacrylamide-based, and/or hydrophilic gel-based materials. Other embodiments may additionally or instead include attachment of a permanent or a single-use acoustic impedance-matched (e.g., acoustic impedance-matched boot coupling 1050) synthetic or natural polymer based material to the transducer surface. The material can include a hydrogel, a silicone-based material, natural oils, fatty-acid based, and/or a polyurethane. The dry couplings 1050, 1070 can have a known thickness, and can include one or more materials, each with a known thickness. In some embodiments, the dry couplings 1050, 1070 have shape memory, and can maintain its dimensions. A shape memory can assist in the layer adhering to a specific topology on the surface of a human. For dynamic coupling, the controller within the transmitter apparatus constantly monitors the level of electro-mechanical transmit impedance to match it for optimal delivery of ultrasound energy into the tissue and through the dry coupling material. Transmit impedance also indicates to the user when the device is decoupled from the tissue surface. In some embodiments, dry couplings 1050, 1070 can be impregnated with lipophilic or hydrophilic material(s) that slowly is expressed between the transducer and the skin tissue surface of the subject. In some embodiments, the dry couplings 1050, 1070 are formed of a material that is temperature sensitive and changes in elasticity, density and sound speed properties over the range 22° C.-38° C. In some embodiments, the dry couplings 1050, 1070 are designed to stand-off the normally self-heating transducer face from skin. In some embodiments, the transmitter and/or the external controller constantly (or periodically) monitors transducer impedance as well as back reflected signal from a tissue layer or the implant to monitor a change of coupling parameters and to adjust the signal accordingly. In some embodiments, the transmitter includes application specific switchable transmitter transducers. For example, the transmitter transducer can include an annular ring transducer, which can have more than one source diameter turned on at a given time.

In some aspects, the USer can use ultrasound as a means of communication between the transmitting and receiving devices. Because ideal implants respond to physiological changes in the patient, the system implements bidirectional communication between the charger and the implant for control and monitoring. As discussed above, this communication can occur using RF signals (e.g., Bluetooth). Alternatively, the acoustic energy (e.g., ultrasound), can be used as the carrier frequency for such communication, which would eliminate the need for a RF antenna, simplifying the implant.

Specifically, it is realized that the transmitter can sense momentary changes in the standing wave ratio, and those changes can be converted to useful data exchange between transmitter and receiver. To produce a large signal-to-noise ratio of the signal coming from the implant, especially at large depths, phase modulation is used instead of amplitude or frequency modulation. Two-way communication is thus established without a transmitter in the implant.

Figure 11:
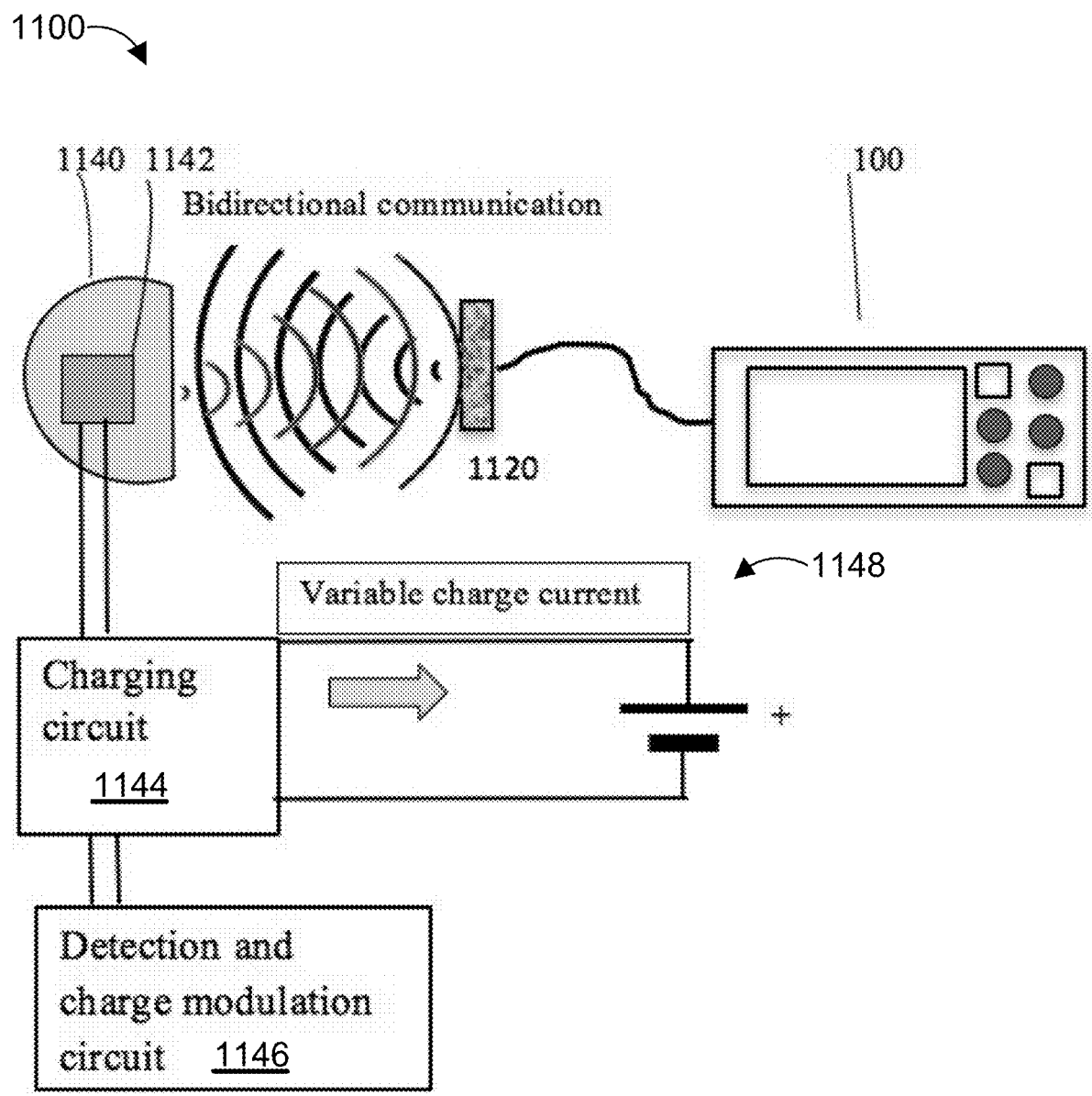
FIG. 11 illustrates a schematic of two-way communication using ultrasound.

FIG. 11 illustrates a schematic 1100 of two-way communication using ultrasound. The acoustic impedance of the receiving transducer 1142 in the implantable receiver 1140 is modulated by modulating the electrical load attached to it in the form of the circuit 1144 that charges the implant battery. As the charge current is momentarily increased 1146 using a detection and charge modulation circuit 1148, the electrical load to the receiving transducer is increased and an acoustical impedance change results. When the charge current returns to the nominal value the transducer impedance is restored. The change in receiving transducer impedance is detected by the transmitting transducer on the transmitter 1120 as backscattered amplitude-shifted keying data transmission.

Figure 12:
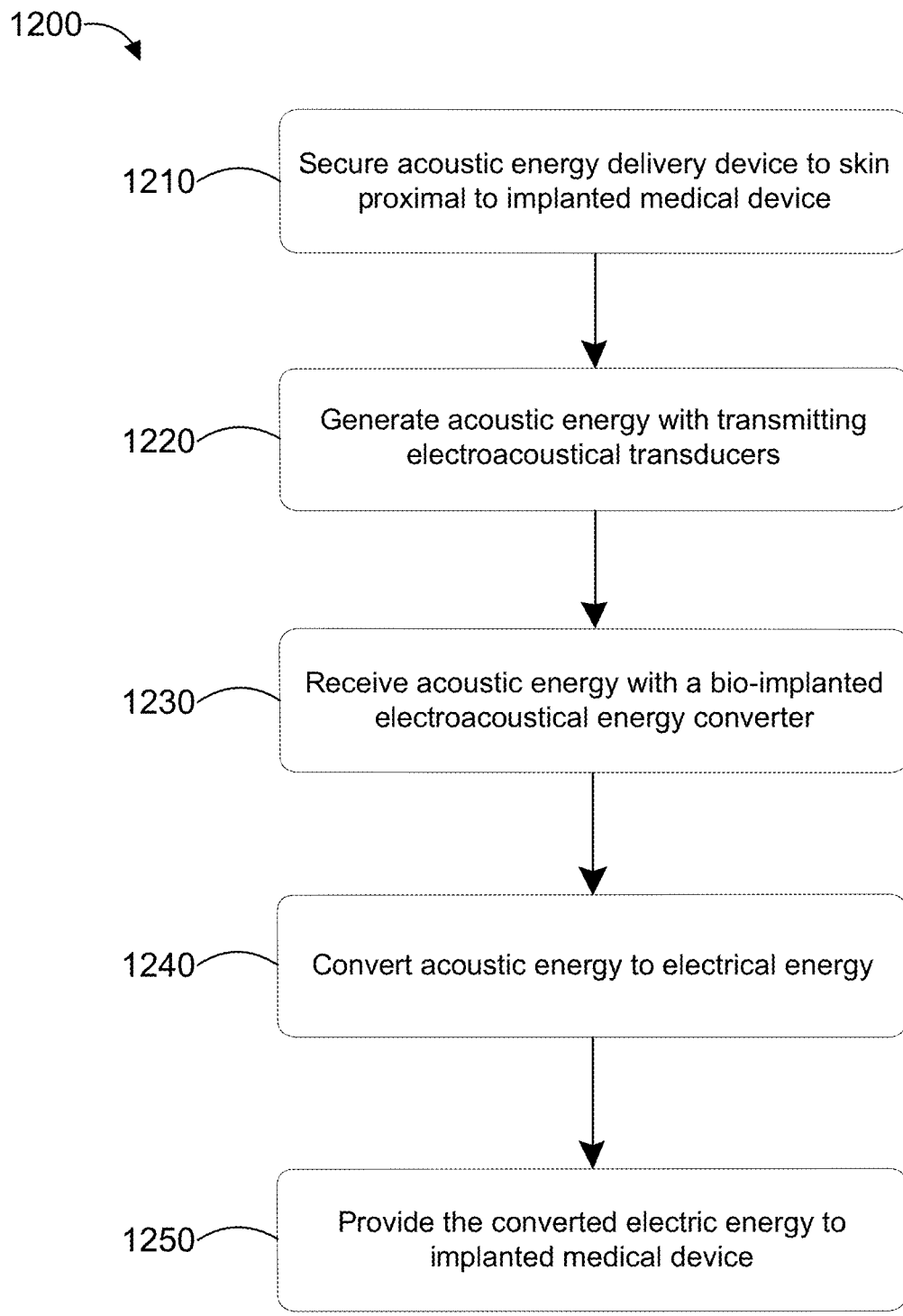
FIG. 12 is a flow chart of a method for providing power to bio-implanted medical device.

FIG. 12 is a flow chart 1200 of a method for providing power to bio-implanted medical device. The method in flow chart 1200 can be performed with any of the devices described herein. In step 1210, an acoustic energy delivery device is secured on a subject's skin tissue, proximal to the bio-implanted medical device. In step 1220, acoustic energy is generated with a multi-dimensional array of transmitting electroacoustical transducers on or in the acoustic energy delivery device. In step 1230, the acoustic energy is received with one or more receiving electroacoustical transducers on or in a bio-implanted electroacoustical energy converter that is electrically coupled to the bio-implanted medical device. In step 1240, the one or more receiving electroacoustical transducers convert the acoustic energy into electrical energy. In step 1250, the converted electrical energy is provided directly or indirectly to the bio-implanted medical device. For example, the converted electrical energy can be stored in a battery in the bio-implanted medical device or in the bio-implanted electroacoustical energy converter.

In the foregoing specification, the invention has been described with reference to specific embodiments. However, one of ordinary skill in the art appreciates that various modifications and changes can be made without departing from the scope of the disclosure and embodiments described herein. Accordingly, the specification and figures are to be regarded in an illustrative rather than a restrictive sense, and all such modifications are intended to be included within the scope of this disclosure.

What is claimed is:

1. A method for providing power to a bio-implanted medical device, the method comprising:
   securing an acoustic energy delivery device on a subject's skin tissue proximal to the bio-implanted medical device;

generating acoustic energy with a multi-dimensional array of transmitting electroacoustical transducers on or in the acoustic energy delivery device;

receiving the acoustic energy with one or more receiving electroacoustical transducers on or in a bio-implanted electroacoustical energy converter that is electrically coupled to the bio-implanted medical device;

providing a wireless feedback signal from the bio-implanted electroacoustical energy converter to the acoustic energy delivery device, the wireless feedback signal corresponding to a magnitude of the acoustic energy received by the bio-implanted electroacoustical energy converter;

adjusting a relative phase of input signals to the multi-dimensional array of transmitting electroacoustical transducers to steer a beam of the acoustic energy based on the wireless feedback signal;

with the one or more receiving electroacoustical transducers, converting the acoustic energy into electrical energy;

providing the electrical energy to the bio-implanted medical device;

receiving, by the acoustic energy delivery device, angular position and translational position data from a gyroscope and an accelerometer disposed on or in the bio-implanted electroacoustical energy converter; and adjusting the relative phase of the input signals to steer the beam of the acoustic energy according to a relative angular position of and a relative translational position of the bio-implantable electroacoustical energy converter with respect to the acoustic energy delivery device.

2. The method of claim 1, wherein the acoustic energy delivery device adjusts an angular or lateral position of a beam of the acoustic energy based on the wireless feedback signal.

3. The method of claim 1, wherein the acoustic energy delivery device adjusts a frequency of the acoustic energy based on the wireless feedback signal.

4. The method of claim 1, wherein the feedback signal is provided by varying an acoustic impedance of the one or more receiving electroacoustical transducers.

5. The method of claim 1, further comprising receiving, by the acoustic energy delivery device, angular position and translational position data from a gyroscope and an accelerometer disposed on or in the acoustic energy delivery device.

6. The method of claim 1, further comprising securing the acoustic energy delivery device on the patient's skin with an acoustically-transparent adhesive.

7. The method of claim 1, further comprising disposing a dry acoustic coupling between the multi-dimensional array of transmitting electroacoustical transducers and the patient's skin.

8. The method of claim 7, wherein the dry acoustic coupling comprises polyurethane, silicone, fatty-acids, poly-acrylamide, a lipophilic material, or a hydrophilic material.

9. The method of claim 7, wherein the dry acoustic coupling includes a dynamic coupling to optimize impedance matching of the transmitting electroacoustical transducers to the dry acoustic coupling.

10. The method of claim 1, further comprising magnetically retaining an alignment of the acoustic energy delivery device and the bio-implanted electroacoustical energy converter with first magnets disposed on a housing of the acoustic energy delivery device and second magnets disposed on the skin tissue or on a housing of the bio-implanted electroacoustical energy converter, the first magnets having an opposite polarity to the second magnets.

11. The method of claim 1, further comprising optimizing alignment of transmitter transducer and receiver transducer faces using an x-y-z and angular alignment mechanical devices.

12. A method for providing power to a bio-implanted medical device, the method comprising:

securing an acoustic energy delivery device on a subject's skin tissue proximal to the bio-implanted medical device;

generating acoustic energy with a multi-dimensional array of transmitting electroacoustical transducers on or in the acoustic energy delivery device;

receiving the acoustic energy with one or more receiving electroacoustical transducers on or in a bio-implanted electroacoustical energy converter that is electrically coupled to the bio-implanted medical device;

providing a wireless feedback signal from the bio-implanted electroacoustical energy converter to the acoustic energy delivery device, the wireless feedback signal corresponding to a magnitude of the acoustic energy received by the bio-implanted electroacoustical energy converter;

adjusting a relative phase of input signals to the multi-dimensional array of transmitting electroacoustical transducers to steer a beam of the acoustic energy based on the wireless feedback signal;

with the one or more receiving electroacoustical transducers, converting the acoustic energy into electrical energy;

providing the electrical energy to the bio-implanted medical device; and receiving, by the acoustic energy delivery device, angular position and translational position data from a gyroscope and an accelerometer disposed on or in the acoustic energy delivery device.

13. The method of claim 12, wherein the acoustic energy delivery device adjusts an angular or lateral position of a beam of the acoustic energy based on the wireless feedback signal.

14. The method of claim 13, further comprising:

adjusting the relative phase of the input signals to steer the beam of the acoustic energy according to a relative angular position of and a relative translational position of the bio-implantable electroacoustical energy converter with respect to the acoustic energy delivery device.

15. The method of claim 12, wherein the acoustic energy delivery device adjusts a frequency of the acoustic energy based on the wireless feedback signal.

16. The method of claim 12, wherein the feedback signal is provided by varying an acoustic impedance of the one or more receiving electroacoustical transducers.

17. The method of claim 12, further comprising securing the acoustic energy delivery device on the patient's skin with an acoustically-transparent adhesive.

18. The method of claim 12, further comprising disposing a dry acoustic coupling between the multi-dimensional array of transmitting electroacoustical transducers and the patient's skin.

19. The method of claim 18, wherein the dry acoustic coupling comprises polyurethane, silicone, fatty-acids, poly-acrylamide, a lipophilic material, or a hydrophilic material.

20. The method of claim 18, wherein the dry acoustic coupling includes a dynamic coupling to optimize impedance matching of the transmitting electroacoustical transducers to the dry acoustic coupling.

21. The method of claim 12, further comprising magnetically retaining an alignment of the acoustic energy delivery device and the bio-implanted electroacoustical energy converter with first magnets disposed on a housing of the acoustic energy delivery device and second magnets disposed on the skin tissue or on a housing of the bio-implanted electroacoustical energy converter, the first magnets having an opposite polarity to the second magnets.

22. The method of claim 12, further comprising optimizing alignment of transmitter transducer and receiver transducer faces using an x-y-z and angular alignment mechanical devices.

* * * * *